(12) United States Patent
Bowen et al.

(10) Patent No.: US 9,617,072 B2
(45) Date of Patent: Apr. 11, 2017

(54) LINED STORAGE BIN

(71) Applicant: Synaptic Wireless, LLC, O'Fallon, MO (US)

(72) Inventors: Charles H. Bowen, O'Fallon, MO (US); P. Mark Bowen, Fayetteville, GA (US)

(73) Assignee: Synaptic Wireless, LLC, O'Fallon, MO (US)

( * ) Notice: Subject to any disclaimer, the term of this patent is extended or adjusted under 35 U.S.C. 154(b) by 26 days.

(21) Appl. No.: 13/796,868

(22) Filed: Mar. 12, 2013

(65) Prior Publication Data

US 2014/0263346 A1 Sep. 18, 2014

(51) Int. Cl.
  *B65F 1/06* (2006.01)
  *B65F 1/16* (2006.01)
  *A61B 50/36* (2016.01)
  *A61B 50/00* (2016.01)
  *A61B 50/30* (2016.01)

(52) U.S. Cl.
  CPC ............ *B65F 1/06* (2013.01); *A61B 50/36* (2016.02); *B65F 1/062* (2013.01); *B65F 1/1607* (2013.01); *A61B 50/30* (2016.02); *A61B 2050/0064* (2016.02); *A61B 2050/0088* (2016.02); *A61B 2050/314* (2016.02)

(58) Field of Classification Search
  CPC . B44D 3/128; B65F 1/06; B65F 1/062; B65F 1/068; B65F 2210/1815; A61B 19/0287
  USPC .......... 220/495.08, 495.11, 908, 908.3, 695, 220/495.04, 908.1
  See application file for complete search history.

(56) References Cited

U.S. PATENT DOCUMENTS

| | | | | |
|---|---|---|---|---|
| 1,984,170 | A | * | 12/1934 | Archbold, Jr. ............... 220/695 |
| 2,720,346 | A | * | 10/1955 | Compton ..................... 222/570 |
| 2,903,154 | A | * | 9/1959 | Hendershot .................. 220/697 |
| 3,329,307 | A | * | 7/1967 | Jacobson ..................... 220/695 |
| 3,454,182 | A | | 7/1969 | Morton |
| 3,722,561 | A | * | 3/1973 | O'Leary et al. ............. 141/316 |
| 4,009,802 | A | * | 3/1977 | Hayduchok .................. 222/108 |
| 4,466,553 | A | * | 8/1984 | Zenger ..................... 220/495.08 |
| D283,492 | S | * | 4/1986 | Nitsch ............................ D9/436 |
| D286,268 | S | * | 10/1986 | Wolff ............................. D9/447 |
| 4,765,579 | A | * | 8/1988 | Robbins et al. .............. 248/101 |
| 4,892,224 | A | * | 1/1990 | Graham ........................ 141/391 |
| 5,065,891 | A | * | 11/1991 | Casey ...................... 220/495.08 |
| D322,221 | S | * | 12/1991 | Neff .............................. D9/435 |
| 5,143,242 | A | * | 9/1992 | Millasich ................. 220/495.02 |
| 5,160,062 | A | * | 11/1992 | Strawder ................. 220/495.08 |
| 5,195,662 | A | * | 3/1993 | Neff .............................. 222/108 |
| 5,269,435 | A | * | 12/1993 | Hallock, III ............. 220/495.08 |

(Continued)

FOREIGN PATENT DOCUMENTS

WO    2005115881 A1    12/2005

OTHER PUBLICATIONS

International Search Report, International Patent Application No. PCT/US14/15358, mailed on May 28, 2014, 10 pages.

*Primary Examiner* — Stephen Castellano
(74) *Attorney, Agent, or Firm* — Lewis Rice LLC

(57) ABSTRACT

Methods and apparatus for maintaining a sanitary disposal and storage bin for consumed medical products using a storage bin with a liner bag and an attached shielding grommet in the shape of a circle flattened on one end which, when soiled, may itself be placed in the liner bag within the container.

13 Claims, 7 Drawing Sheets

(56) References Cited

U.S. PATENT DOCUMENTS

| | | | | |
|---|---|---|---|---|
| 5,299,708 A * | 4/1994 | Hallock, III | ............ | 220/495.08 |
| 5,320,241 A * | 6/1994 | Evans | ............ | 220/495.09 |
| 5,322,179 A * | 6/1994 | Ting | ............ | 220/495.07 |
| 5,385,251 A * | 1/1995 | Dunn | ............ | 215/11.3 |
| 5,403,634 A * | 4/1995 | Mauffette | ............ | 428/34.3 |
| 5,503,292 A * | 4/1996 | Cuccharia | ............ | 220/495.07 |
| 5,505,334 A * | 4/1996 | Triglia | ............ | 221/199 |
| D377,554 S * | 1/1997 | Adriaansen | ............ | D34/7 |
| 5,615,809 A | 4/1997 | Feer et al. | | |
| 5,628,424 A * | 5/1997 | Gola | ............ | 220/495.07 |
| 5,634,566 A | 6/1997 | Jansen et al. | | |
| 5,779,093 A * | 7/1998 | Poole et al. | ............ | 220/698 |
| D432,421 S * | 10/2000 | Sullivan, Jr. | ............ | D9/440 |
| 6,199,718 B1 * | 3/2001 | Ellis | ............ | 220/735 |
| 6,213,338 B1 * | 4/2001 | Cogdill | ............ | 220/700 |
| 6,378,721 B1 * | 4/2002 | Williams | ............ | 220/495.08 |
| D457,700 S * | 5/2002 | Acord | ............ | D32/54 |
| D489,261 S * | 5/2004 | Doelling | ............ | D9/447 |
| D494,470 S * | 8/2004 | Guyot | ............ | D9/447 |
| 6,824,005 B1 * | 11/2004 | Ashinhurst | ............ | 220/495.07 |
| D509,427 S * | 9/2005 | Townsend | ............ | D9/447 |
| RE39,726 E * | 7/2007 | Lin | ............ | 220/263 |
| 7,364,049 B2 | 4/2008 | Panek, Jr. | | |
| D664,320 S * | 7/2012 | Sakko | ............ | D32/54 |
| 8,317,055 B2 * | 11/2012 | Zawrotny et al. | ............ | 220/495.07 |
| 8,740,012 B2 * | 6/2014 | Ekkert | ............ | 220/698 |
| 8,752,706 B2 * | 6/2014 | Dermo | ............ | 206/561 |
| 2005/0056649 A1 * | 3/2005 | Simonson | ............ | 220/495.08 |
| 2006/0283863 A1 * | 12/2006 | Coles | ............ | 220/495.08 |
| 2007/0084866 A1 * | 4/2007 | Saeugling | ............ | 220/495.06 |
| 2008/0264948 A1 * | 10/2008 | Kovacevich et al. | ............ | 220/495.08 |
| 2010/0230413 A1 * | 9/2010 | Crudgington, Jr. | ............ | 220/495.02 |
| 2011/0168718 A1 * | 7/2011 | Tsai et al. | ............ | 220/495.08 |
| 2012/0217247 A1 * | 8/2012 | Adkins et al. | ............ | 220/495.08 |

* cited by examiner

LINED STORAGE BIN

BACKGROUND

1. Field of the Invention

This disclosure relates to systems and methods for disposing of contaminated equipment and supplies, in particular to a lined storage bin which vents air trapped by a liner bag to the environment.

2. Description of the Related Art

Sanitation and sterilization are important to preventing infection and disease in medical practice, particularly in the typical environment where a medical facility and its equipment are used to treat a series of patients. Each treatment may result in the generation of medically contaminated materials ranging from tongue depressors and plastic thermometer covers to surgical towel, gloves, and smocks soiled with bodily fluids from a patient undergoing emergency surgery in an operating room. These materials pose a risk of disease and infection to both the attending staff and future patients treated in the same facility using the same equipment, and both the treatment rooms and equipment are normally sterilized and sanitized before the next patient is treated.

To this end, soiled or potentially contaminated equipment is generally sequestered in disposal bins specially marked as containing contaminated materials. These materials may be items that are intended to be used once on a single patient and then permanently discarded, or equipment that may be sterilized and used again on a subsequent patient. Ideally, after treatment concludes, the treatment room is cleaned and sterilized, and the bag lining the disposal bin is sealed and safely discarded, and a new bag is placed in the disposal bin.

In many contexts, particularly the fast-paced environment of an emergency department or a delicate surgical operation, the doctor, nurses, and staff often do not have time to carefully isolate biologically contaminated materials in conventional storage containers, which are sometimes impractical in this setting for several reasons. The top of such containers must be open-faced so that contaminated materials may be quickly and easily placed into them. However, because the attending personnel are generally moving quickly, they do not have time to carefully place the materials in the bin. Instead, at best, the materials are hastily dropped into the bin, which causes the materials to come into contact with the lip or rim of the container, contaminating it with the very biological material that the container is meant to sequester.

Once the container itself is contaminated, it ceases to serve its purpose unless thoroughly cleaned and sanitized, which costs time and money, assuming it is done at all. If the technicians or other staff responsible for cleaning the operating room neglect to clean the bin, the contaminated container will be used again with the next patient, exposing that patient— and the attending staff— to biological materials from the last patient, thus increasing the risk of infection and disease to both staff and future patients using the operating room.

Ordinarily, this problem would be solved by lining the disposal bin with a flexible liner, such as a sterilized plastic bag. The bag is placed in the bin and the open end of the bag is inverted to cover the rim of the storage bin, similar to a typical residential kitchen trash can. Thus, when biologically contaminated products are deposited in the waste disposal bin, even if some of the biological material comes into contact with the rim, the rim is covered by the plastic bag. When the bag is removed from the bin and sealed, the portion of the bag that was exposed to the contaminated material will be within in the interior of the bag, sequestering the contaminated materials.

However, this solution also presents its own set of problems. First, when a liner bag is placed over the rim, pockets of air generally remain in the bin between the interior surface of the bin and the exterior surface of the bag. When materials are discarded into the bin, the volume of the materials displaces some of the trapped air. Because materials are typically dropped into the bin, this displacement is usually very rapid. Because the containers are typically enclosed except for the central opening, the only major route for the displaced air to flow through is between the exterior of the bag and interior of the bin, ultimately venting into the environment through the opening in the bin by passing between the bag and the rim.

Because the material discarded rapidly displaces the air, the air in turn rapidly ventilates, often dislodging the bag from the rim, which slips partially or completely into the interior of the bin. This then leaves the rim exposed when the next item is discarded, and the doctors and nurses often cannot and should not pause mid-procedure to reattach the bag. The problem is thus worse— not only is the bin exposed to contamination, but the bag that has fallen into the container is also exposed and the exterior of the bag may become contaminated. The staff then must not only safely dispose of the biological material in the container, but also must dispose of the contaminated bag.

This problem might be addressed by fitting a smaller bag to the container so that the fit between the bag and rim is snug, preventing the bag from slipping into the container. However, this only substitutes one problem for another. The tighter fit generally cuts off the primary ventilation route for trapped air. When material is thrown into such a bag, the displaced air is trapped with no escape route, and the total volume available for the air decreases with each item that is thrown into the bin. This places the air under increasing pressure, forcing it to relocate to the area of the bin where it can most expand to equalize pressure with the air in the environment. Because the material in the bag accumulates at the bottom of the bin, the trapped air generally accumulates near the top of the bin, exerting increasing pressure on the exterior of the bag, causing it to collapse and "puff in" from the perception of the user.

As material accumulates in the container, the volume available for the trapped air to occupy decreases and the air pressure on the exterior of the bag increases, further exaggerating the "puffing in" phenomenon. Eventually, the air pressure will either cause the bag to pop or force it off the rim, despite the tighter connection. Either situation reintroduces the problems the bag was meant to solve, as well as the problem of removing a soiled bag. The puffing effect also reduces the amount of available volume within the bag, causing the container to appear "full" even though there is unused storage volume within the bin occupied by the trapped air.

Further, the smaller bag stretched over the rim to achieve a tighter seal is under increased stress, weakening the bag and increasing the risk of a tear, particularly as objects with edges—even blunt edges— are thrown into the container. For example, where the bin is used to hold materials such as a surgical clamp, if a clamp is even gently dropped into the storage bin and impacts the rim, the thinly stretched plastic bag will be caught in the impact between the clamp and the rim. Because the smaller bag is more tightly stretched, the likelihood of the bag tearing in this impact is higher. If the bag tears, the rim of the container is once again exposed to contamination and the bag itself is no longer self-contained when closed. Thus, the entire system doesn't work, as the container becomes contaminated despite the bag, and the ripped bag is no longer effective at sequestering the contaminated tools or materials stored within it. Similarly, the puffing effect stretches the portion of the bag within the interior of the container, providing an increased surface area to contact discarded materials and giving the bag less flexibility to yield as discarded materials descend into the bin. This in turn also increases the risk of rips or tears in the bag.

This problem might be partially solved by including a shield or grommet which both holds the bag in place around the rim and protects it from being torn by discarded materials impacting the rim. However, this fails to address the problems caused by trapped air and introduces yet further problems. Instead of a contaminated rim that must be re-sterilized and sanitized before each use, the grommet must be sterilized or replaced. Further, to remove the bag from the container, the grommet first must be removed and set aside. If the contaminated grommet is placed on another surface, that surface may become contaminated and require cleaning and sterilization as well. In the fast-paced environment of a medical services facility, there exists a reasonable likelihood that the staff cleaning the room will not appreciate, or simply overlook, that this surface is now contaminated and must be re-sterilized, thus re-introducing the problem of exposing the next patient to contaminated materials from a prior patient. Also, by temporarily placing the grommet somewhere else, there is a risk that the grommet will be forgotten in the haste to clean and sterilize the room, thus leaving a contaminated item in the room, and re-introducing the very risk of infection and disease that the bin is meant to reduce.

SUMMARY

Methods and apparatus for maintaining a sanitary disposal and storage bin for consumed medical products using a storage bin with a liner bag and an attached shielding grommet in the shape of a circle flattened on one end which, when soiled, may itself be placed in the liner bag within the container.

There is described herein, among other things, a storage bin comprising: a container having a closed base end and an opposing open top end with an elongated body therebetween, the open top end having a rim circumscribing a generally circular opening providing access to the interior of the enclosed container; a venting grommet attachable to the open top end comprising: an outer wall having opposing top and bottom sides and being generally in the shape of a circular major arc having two terminal ends, the outer wall having a radius larger than the radius of the rim; an inner wall having opposing top and bottom sides and being generally in the shape of a circular major arc the endpoints of which are connected by a chord coplanar with the terminal ends of the outer wall, the inner wall having a radius smaller than the radius of the rim and the inner wall being generally concentric with and circumscribed by the outer wall; a top generally perpendicularly and terminally connected to the top side of the outer wall and the top side of the inner wall; and, wherein when the venting grommet is attached to the open top end of the container, a portion of the rim circumscribes the inner wall and the outer wall circumscribes a portion of the rim; wherein when the venting grommet is rotated about ninety degrees with respect to the generally circular opening, the venting grommet can pass through the generally circular opening.

In an embodiment, the storage bin further comprises: a liner bag having an open end wherein when the liner bag is disposed upon the container such that the open end of the liner bag circumscribes the rim and when the venting grommet is attached to the container, the venting grommet holds the liner bag in place.

In an embodiment of the storage bin, the rim and the outer wall are threaded such that the venting grommet may be screwed unto the rim.

In an embodiment of the storage bin, the storage bin further comprising: the container having an interior surface; and, a liner bag dispensing system comprising: a spindle within the container having opposing top and bottom ends and an elongated body therebetween, the bottom end of the spindle attached to the center of the base end of the container; a support within the interior having opposing top and bottom sides, the top end of the spindle being attached to the support; wherein when a spool of liner bags is placed on the spindle, a liner bag from the spool of liner bags can pass between the support and the interior surface of the container.

In an embodiment, the storage bin further comprising a spool of liner bags disposed on the spindle.

In an embodiment of the storage bin, the length of the spindle is less than half the length of the enclosed container.

In an embodiment of the storage bin, the support is removable from the spindle.

In an embodiment of the storage bin, the height of the inner wall is about the same as the height of the outer wall.

In an embodiment of the storage bin, the radius of the rim is less than the radius of the cylindrical container.

In an embodiment of the storage bin, the venting grommet is made from plastic.

In an embodiment of the storage bin, the distance between the center of the chord and the midpoint of the major circular arc of the outer wall is greater than the radius of the rim and less than the diameter of the rim.

In an embodiment of the storage bin, the distance between the center of the chord and the midpoint of the major circular arc of the outer wall is large enough that the venting grommet cannot pass through the rim into the container unless the rim is deformed into a generally ellipsoid configuration having a major axis greater than the diameter of the rim when the rim is not deformed.

There is also described herein a storage bin comprising: a container defining an interior space and having a rim circumscribing an opening in the container providing access to the interior space; a bag having opposing open and closed ends and being disposed upon the container such that the closed end is within the interior space and the open end circumscribes the rim such that air can flow out of the interior space between the bag and the rim; a venting grommet sized and shaped for attaching to the rim such that when the grommet is attached to the rim the grommet holds the bag in place and leaves a sufficient portion of the bag uncovered that air in the interior space displaced when an object is inserted into the bag can flow out of the interior space between the bag and the rim at the sufficient uncovered portion.

There is also described herein a method for maintaining a sanitized waste disposal bin comprising the steps of: providing a sanitized waste disposal bin comprising: a generally cylindrical container having a hollow interior and a rim circumscribing an opening at one end of the container; a liner bag having opposing closed and open ends, the end disposed on the container such that the open end circumscribes the closed end is within the hollow interior; a venting grommet having a central opening and attached to the one end such that the liner bag is between the rim and the venting grommet; placing refuse in the liner bag through the central opening of the venting grommet attached to the container; removing the venting grommet from the one end; placing the venting grommet in the liner bag within the hollow interior through the rim; removing the liner bag containing the venting grommet from the container; disposing of the liner bag containing the venting grommet; and maintaining a sanitized waste disposal bin.

In an embodiment, the method, further comprising: providing a spool of liner bags within the hollow interior, the spool including a second liner bag having an open end attached to the closed end of the liner bag; providing a second venting grommet; detaching the liner bag from the second liner bag; disposing the second liner bag on the container such that the open end of the second bag circumscribes the rim; and attaching the second venting grommet to the rim such that the second liner bag is between the rim and the second venting grommet.

DESCRIPTION OF THE PREFERRED EMBODIMENTS

Figure 1:
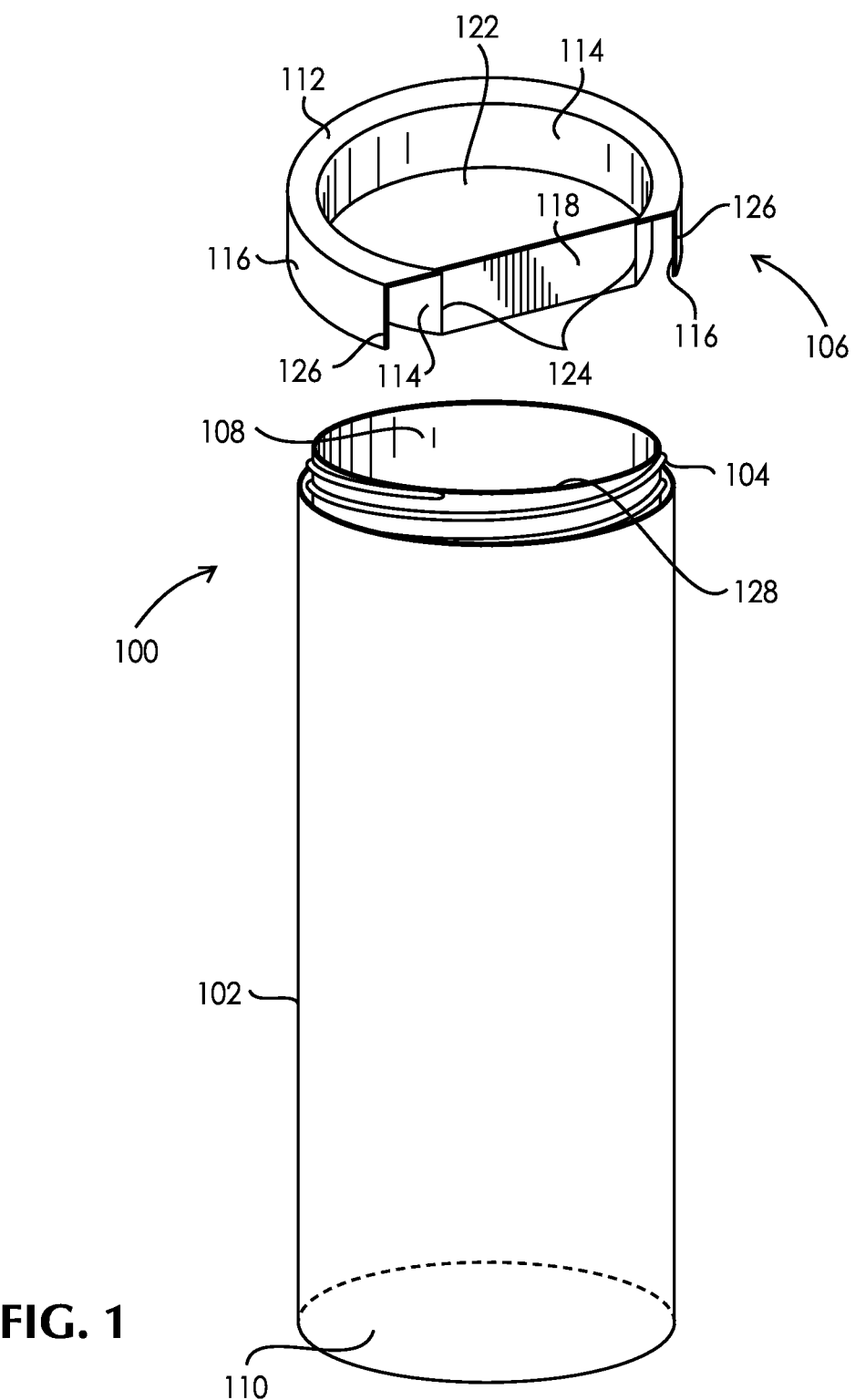
FIG. 1 provides a side elevation view of one embodiment of a lined storage bin and venting grommet.
Figure 2:
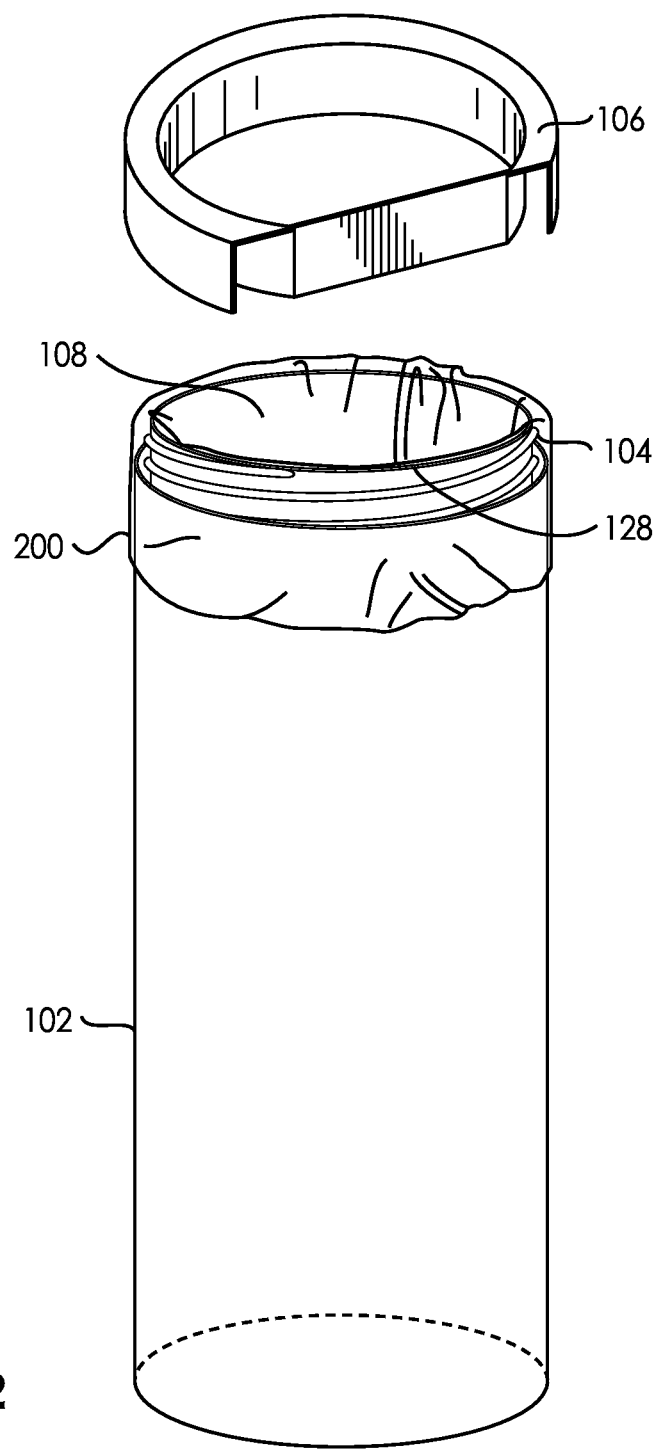
FIG. 2 provides a side elevation view of a lined storage bin including a sanitary disposal bag, and a venting grommet.

The systems, devices, and methods described herein generally include a lined storage bin comprising a container, a venting grommet, and a liner bag. In an embodiment, the systems, devices, and methods may further comprise a bag storage and dispensing system. The venting grommet is generally sized and shaped to provide a ventilation route for trapped air to escape rapidly from the storage container when displaced by the volume of items disposed in the bin. The venting grommet also generally holds the liner bag in place while also permitting a loose enough fit between the liner bag and the rim that sufficient air may rapidly escape through the ventilation route by passing between the liner bag and the rim without dislodging the bag from the rim.

Such systems can be particularly useful for the storage of medical reuseables, particularly items that may be used multiple times at different points on the same procedure with one patient, but which need to remain sterile (other than for contact with that one patient) during the procedure. They may then be traditionally resterilized or disposed of. These types of devices generally need a semi-sterile location to be placed during the procedure, semi-sterile in that the location is clean with regards to contact with body fluids from other patients, but not clean with regards to body fluids from this patient. The devices also need to remain easily accessible to the person performing the procedure. As a non-limiting example, a medical device such as a surgical clamp may be in this category. The same clamp may be used at multiple points during a procedure without it needing to be cleaned or resterilized (since all contamination is from this patient). However, the clamp cannot be placed on a non-sterile surface or storage device during the procedure, as then it could not be reused with this patient.

Although the present disclosure is generally in conjunction with storing medically contaminated products, tools, or materials, one of ordinary skill in the art will understand this disclosure to encompass other uses for the systems, devices, and methods described herein. The present disclosure is suitable for use in any setting in which it is desirable that a material or tool be sequestered or isolated. By way of example and not limitation, the present disclosure is suitable for use with materials that are, become, or are exposed to, radioactive compounds or materials. Such embodiments may include additional or modified components, including but not limited to liners designed for use in sequestering radioactive materials.

The devices, systems, and methods described herein generally include a storage container, a venting grommet, and one or more bag liners. The devices, systems, and methods described herein also generally include the disposing of potentially contaminated objects by placing such objects in a liner bag lining the interior of a storage container by inserting the objects through the central opening in a venting grommet attached to the rim of the storage container, and placing the venting grommet itself in the liner bag before removing the liner bag from the storage container.

In the depicted embodiment of FIG. 1, an exploded view of a storage bin (102) and a venting grommet (106) is provided. The depicted storage bin (102) is a generally cylindrical container having a hollow interior and two ends (108) and (110), one of which is an open end and the other of which is a generally solid base (110). When the bin (102) is placed for use, the base (110) is normally in contact with the surface on which the bin (102) rests, and the base (110) is generally flat so that the bin (102) stands upright when placed on a flat surface.

In the depicted embodiment, the base (110) is generally sized and shaped similarly to the cross-section of the bin (102) and constructed from the same or similar materials. However, in an embodiment, the base (110) may be sized and shaped differently, such as for fitting into a particular holder designed to accommodate a bin (102), and constructed from or include materials different from those use to construct the bin (102) and/or its subcomponents.

In an embodiment, the base (110) may include a weighting system (not depicted). In such an embodiment, the weighting system moves the center of gravity of the device closer to the surface on which it rests and thus reduces the likelihood of tips, spills, or otherwise dislodging the device from its resting place if jostled or disturbed.

In an alternative embodiment, the base (110) may include a system (not depicted) for increasing the coefficient the friction between the base (110) and the surface on which it rests, also to reduce spills, tips, and dislodging. Such a system may include, without limitation: rubber feet; a friction pad; a friction coating; texturing, shaping, or sizing to increase friction; adhesive; the use of magnets or magnetism; or other systems.

The depicted bin (102) includes a top end opposite the base (110) which has an opening (108) allowing access to the hollow interior of the bin (102). In the depicted embodiment, the top end is narrower than the base (110), forming a second cylindrical shape having a smaller radius than the bin (102) and attached to the bin (102) at the top end. In the depicted embodiment, the exterior of the storage bin (102) near the opening end (108) is threaded (104) such that a threaded venting grommet (106) may be secured to the storage bin (102) by counter-rotating the bin (102) and/or grommet (106) so that the threads (104) of the bin (102) interlock with the threads in the venting grommet (106).

The cylindrical shape of the storage bin (102), particularly the threaded portion (104), allows a threaded venting grommet (106) to be gently coupled to the storage bin (102). Generally speaking, in an embodiment including a threaded interlocking system, the edges of the threads (104) are not sharp, but rather are smooth and rounded to reduce the likelihood that a bag retained between the threads (104) will be damaged or torn when the venting grommet (106) is attached to the storage bin (102).

Although the body of the storage bin (102), as depicted, is generally cylindrical, other shapes and configurations are possible and specifically contemplated, including without limitation polygonal prisms and ellipsoidal configurations. The diameter of the depicted storage bin (102), as well as the height, may vary from embodiment to embodiment, generally depending upon the type of materials or tools with which a given embodiment is to be used.

By way of example and not limitation, where an embodiment is to be used for a lengthy surgical procedure, a larger bin (102) may be necessary to contain all of the disposed materials and/or tools, whereas a smaller bin (102) may suffice for a shorter or less complex procedure. By contrast, in an embodiment for use in an examining room in a family practice clinic, the bin (102) may primarily hold discarded ear swabs, tongue depressors, plastic slip shields, latex gloves, and the like, and a bin (102) with a shorter height or smaller diameter may be sufficient to accommodate the volume of material accumulated.

Similarly, the diameter of the opening (108) will be sized and shaped to accept the materials and/or tools with which the bin (102) is to be used. In general, the diameter of the opening (108) is large enough to allow the materials to enter the storage bin (102) through the opening (108), but the opening will generally be larger than this to provide a larger target into which users can drop materials, thus improving ease-of-use and reducing the amount of contaminated material that contacts the grommet (106).

In the depicted embodiment of FIG. 1, the top opening (108) is about the same diameter as the body of the storage bin (102). This configuration improves the usage of the interior space of the storage bin (102) because the opening (108) is about the same diameter as the bin (102), and the opening (108) can accommodate the passage of items that are also nearly as large as the diameter of the storage bin (102). This is particularly useful where the items to be inserted are not flexible and cannot be bent or deformed to fit through the opening (108).

The storage bin (102) will generally be made of a material known to one of ordinary skill in the art to be suitable for use in cleaning, sterilization and sanitation procedures for the industry or setting in which a given embodiment is to be used. For example, bins (102) for use in medical facilities will generally be made from smooth plastics, stainless steel, porcelain, or other non-porous solids readily cleanable and sterilizable through use of chemicals and other treatments, including without limitation heat and steam.

The apparatus generally also includes a venting grommet (106), such as the embodiment of a venting grommet (106) depicted in FIGS. 1, 2, 5, 6A, 6B, and 7. In the depicted embodiment of FIG. 2, the venting grommet (106) is sized and shaped for attaching to the open end (108) of the bin (102) such that the grommet (106) generally circumscribes the rim. In the depicted embodiment, the venting grommet (106) is generally in the shape of a flat tire.

The venting grommet (106) serves a number of roles. First, the grommet (106) couples to the bin (102) to hold a liner bag (200) in place. The snugness of the fit between the bag (200) and rim (128) generally is loose enough that air within the bin (102) can, when displaced by objects placed in the bin (102), escape from the bin (102) by passing between the bag (200) and rim (128). This fit is generally loose enough that the force of an item disposed in the bin (102) could dislodge the bag (200) from the rim (128), or the force of the rapid ventilation of the air could itself dislodge the bag (200) from the rim (128). The grommet (106) facilitates the ventilation of air from the bin (102) by, among other things, allowing the bag (200) to be disposed on the rim (128) with a sufficiently loose fit to allow ventilation, while holding the bag (200) in place so that it does not slip into the bin (102) when items are placed in it.

The grommet (106) also provides a rigid shield protecting the rim (128) so that materials dropped or thrown into bin (102) do not puncture, tear, or otherwise damage the liner bag (200). Further, the grommet (106) provides a filter of appropriately sized items to place in the bin (102)—objects which are too large to fit through the central opening (122) in the grommet are large enough to pose a heightened risk of tearing or puncturing the bag (200) when the bag (200) is removed from the container (102).

The "flat tire" shape of the depicted venting grommet (106) is formed from a generally circular major arc closed at the end points (124) via a chord (118). The grommet (106) includes a generally circular major arc-shaped inner wall (114 and an outer wall (116), also generally in the shape of a circular major arc. The outer wall (116) generally has a larger radius (612) than the inner wall (114) and is generally concentric with and circumscribes the inner wall (114). These two walls (114) and (116) are generally the same thickness and height and are connected at the top end (112), so that the cross-section of the structure is generally that of an inverted square U-shape as depicted in FIG. 6B. This U-shape provides a channel or pocket sized and shaped to accommodate, accept, and couple with the rim (128) of the bin (102).

The flat portion (118) of the flat tire shape is generally a flat surface or chord (118) connecting the end points (124) of the interior wall (114). In the depicted embodiments, this flat surface (118) does not extend to the outer wall (116), but rather ends at end points (124), to present the inverted square U-shape cross-section for coupling the grommet (106) to the rim (128). This surface (118) is generally a flat elongated rectangular prism with a height about the same as that of walls (114) and (116). Among other things, this element (118) provides additional rigidity and stability to the grommet (106) so that it maintains its shape.

Figure 7:
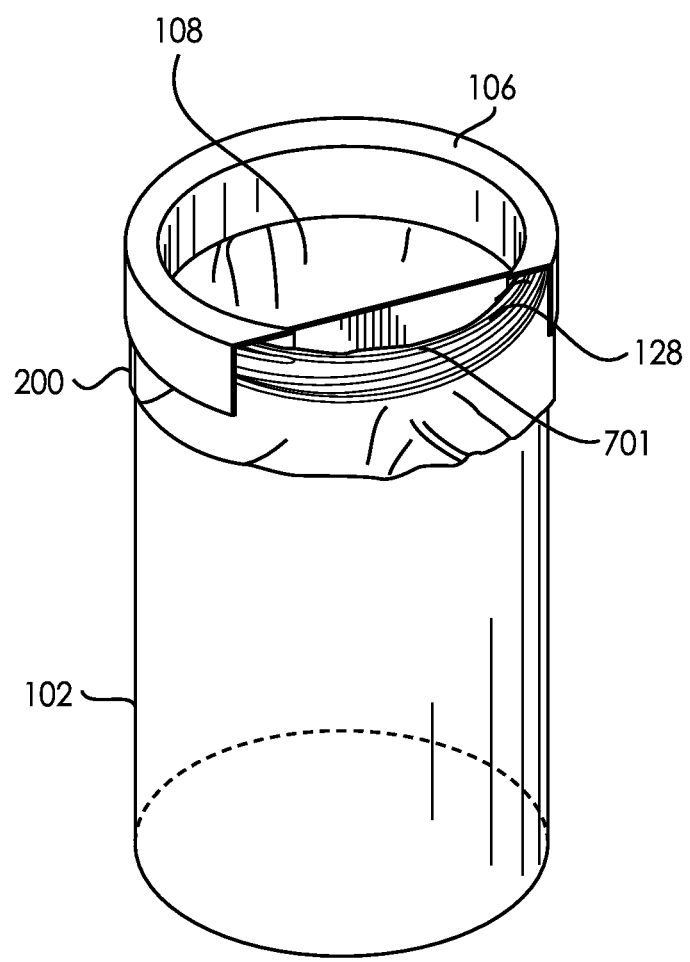
FIG. 7 provides a perspective view of a lined storage bin disposal bag, and a venting grommet, including a sanitary disposal bag, and a venting grommet, with the venting grommet attached to the bin.

As depicted in FIG. 7, the flat portion (118) also results in a portion of the bag (200) disposed upon the rim (128) to be uncovered (701) by the grommet (106). If the fit between the bag (200) and rim (128) is sufficiently loose, air between the bin (102) and the bag (200) can escape from the bin (102) by passing between the bag (200) and the rim (128) at this uncovered portion (701), but there is little risk of the bag (200) becoming dislodged from the rim (128) or otherwise slipping into the bin (102) because the circular portion of the grommet (106) holds the bag (200) in place along the majority of the circumference of the rim (128). Thus, when an object is placed in the bag (200), the volume of the object displaces a volume of air within the bin (102), and that volume of air can vent from the bin (102) without disturbing the bag (200).

Figure 5:
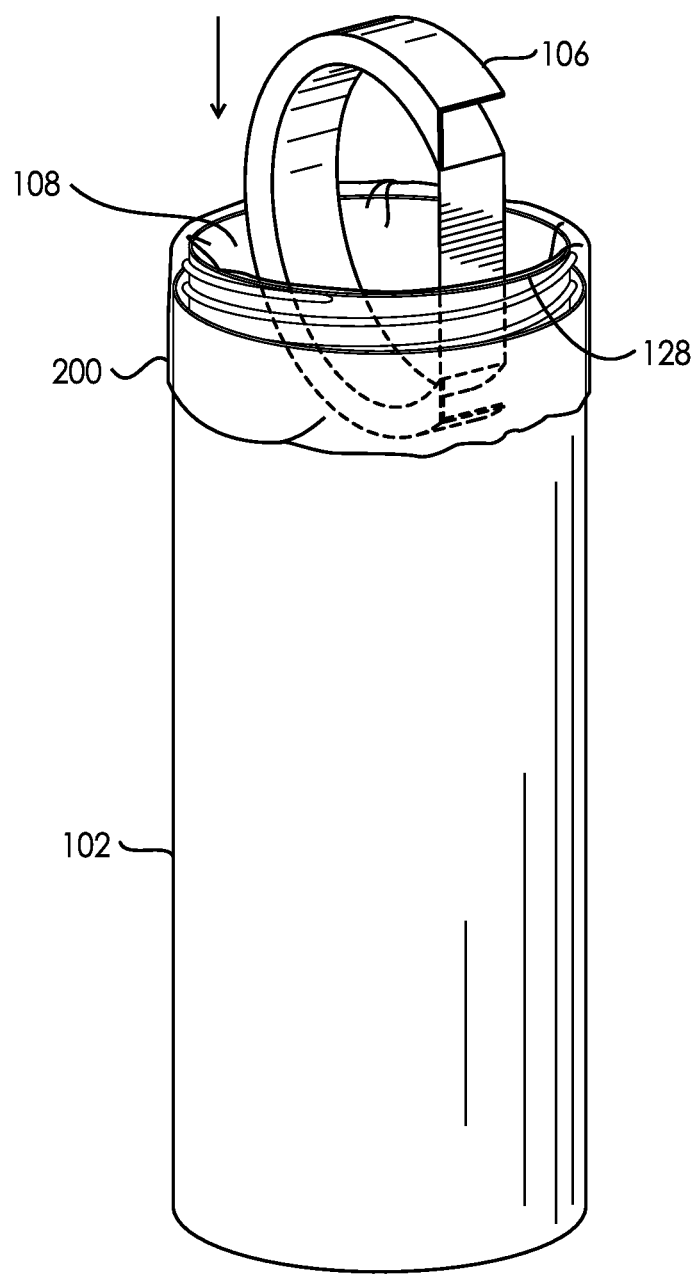
FIG. 5 provides a side elevation view of an embodiment of a venting grommet being inserted into an embodiment of a lined storage bin including a sanitary disposal bag.

The flat chord (118) also allows the grommet (106) to both circumscribe a majority of the rim (128), which in turn circumscribes the opening (108), while also presenting a sufficiently narrow cross-section to, when rotated along a line generally perpendicular to the plane of the chord (118), pass through the opening (108) into the interior of the bin (102), as depicted in FIG. 5. Because the arc-shape leaves a portion (701) of the bag (200) exposed, as depicted in FIG. 7, the chord (118) also provides some protection to the portion (701) of the rim (128) and bag (200) left uncovered by the grommet (106).

In this fashion, the grommet (106) can itself be placed into the bag (200) lining the bin (102). This has the advantage that a soiled or contaminated grommet (106) need not be placed on and contaminate another surface while the bag (200) is being removed from the bin (102), but rather can be removed and placed directly into the bag (200). Also, because the grommet (106) need not be set aside to change the bag (200), cleaning staff are unlikely to leave a soiled grommet (106) in the treatment room, and thus the risk that subsequent treatments or procedures in that room will be exposed to a contaminated grommet (106) is reduced. This also allows a soiled grommet (106) to be placed in the bag (200) while the bag (200) is still disposed upon the rim (128), meaning the soiled grommet (106) is less likely to contaminate the bin (102) itself when the bag (200) is being changed, as the grommet (106) is itself sequestered prior to removing the bag (200).

Figure 6A:
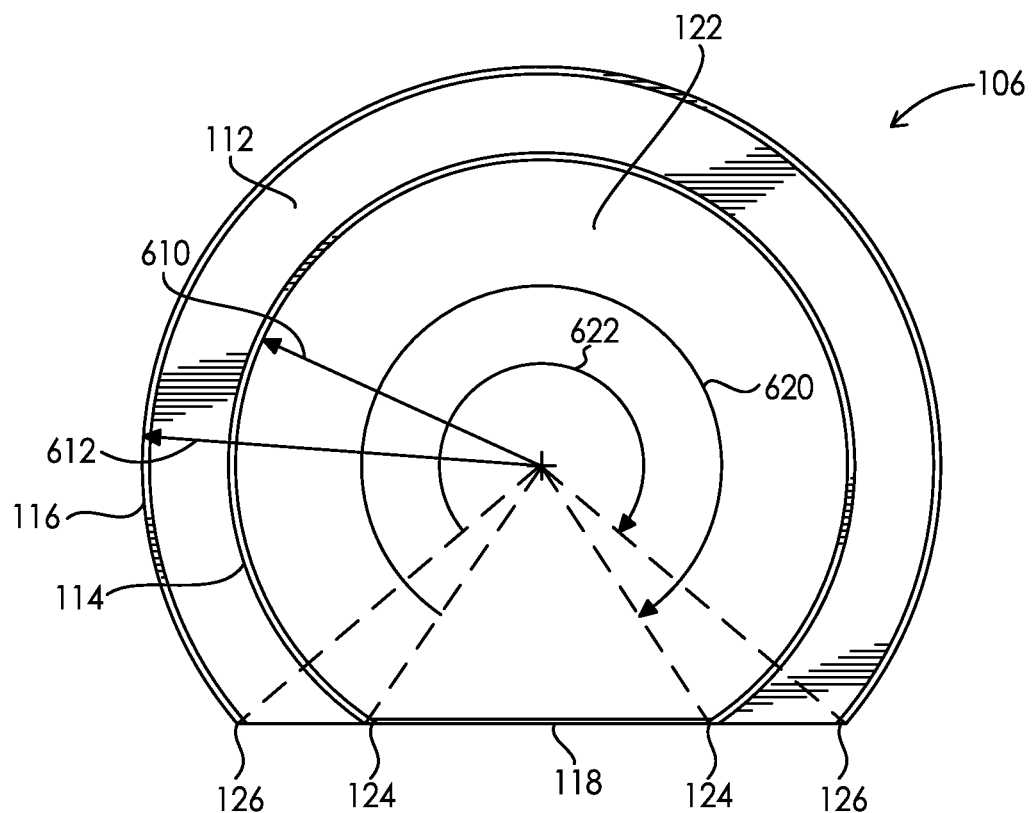
FIG. 6A provides a bottom elevation view of an embodiment of a venting grommet.
Figure 6B:
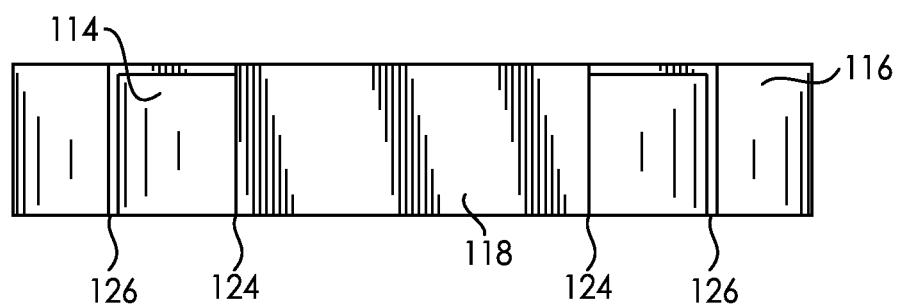
FIG. 6B provides a front elevation view of an embodiment of a venting grommet.

In the depicted embodiment of FIGS. 6A and 6B, some details of the venting grommet (106) are provided. FIG. 6A is a bottom elevation view of venting grommet (106). As depicted, the interior wall (114) is generally in the shape of a circular arc closed at the end points (124) by a generally flat rectangular prism (118), and generally circumscribed by the exterior wall (116). The exterior wall (116), unlike the interior wall (114), does not include a closing surface between the end points (126), again so that the cross-section provides the square inverted U-shape for coupling the grommet (106) to the rim (128). The angle (620) of the arc of the interior wall (114) is generally slightly larger than the angle (622) of the arc defining the external wall (116). The radius (610) of the arc defining the interior wall (114) is less than that of the radius (612) defining the arc of the exterior wall (116). As depicted, the arc shape is the major arc between end points (124), not the minor arc. In the depicted embodiment, the end points of walls (114) and (116) are generally coplanar with chord (118), producing the "flat tire" shape of the grommet (106) when viewed from the top or bottom.

The grommet (106) includes a central opening (122) as depicted in FIGS. 1 and 6, circumscribed in part by walls (114) and (116), through which discarded material is inserted into the storage bin (102) when the device is assembled, as depicted in FIG. 7. In an embodiment, device is assembled by placing a liner bag (200) within the storage bin (102) and then inverting an open end of the liner bag (200) around the opening (108) in the top of the storage bin (102) and dragging the liner bag down around the outside surface of the rim (128), similar to how garbage bags are attached to garbage cans in ordinary domestic use. The liner bag (200) effectively provides a sanitary shield which prevents the rim (128) of the opening (108) from coming into contact with biological material, thus reducing the need to sanitize or clean the rim (128).

Items placed in the bag (200) may pull the bag (200) into the container (102), causing a portion of the bag (200) situated outside of the container (102) to slip inside the container (102), effectively eliminating the shielding function of the bag (200). As described elsewhere herein, the venting grommet (106) may be attached to the top of the storage container (102), sandwiching the bag (200) between the grommet (106) and the rim (128), to hold the bag (200) in place and reduce the likelihood of such slippage by holding the bag (200) in place.

In an embodiment, the venting grommet (106) may be twisted to engage threads (104) on the rim (128) with threads on the venting grommet (106), establishing a more secure connection between the container (102) and the venting grommet (106). In an alternate embodiment, the venting grommet (106) is sized and shaped to attach to the rim (128) without the use of threads, and is held in place through friction between walls (114) and (116) and rim (128). The assembled embodiment depicted in FIG. 7 shows a bag (200) installed in the storage bin (102) and held in place a venting grommet (106) placed over the rim (128) of the bin (102). Contaminated materials may be placed into the storage bin (102) by inserting such materials through the opening (108) and venting grommet (106). The venting grommet (106) will also reduce the likelihood of tearing or ripping of the bag (200) or cracking or damaging the rim (128).

To minimize the amount of the rim (128) which will be exposed (701) when the grommet (106) is attached, the grommet (106) may be sized, shaped, and configured to achieve a long arc-length of walls (114) and (116) while still sizing and shaping the grommet (106) to be capable of being inserted through opening (108) when rotated about 90 degrees around an axis generally perpendicular to chord (118), as depicted in FIG. 5. The longer the arc-length of the walls, the smaller the uncovered portion (701) of the bag (200) and/or rim (128) as seen in FIG. 7. However, as the arc-length of walls (114) and (116) approaches 360 degrees, i.e. a circle, the maximum length of the cross section of the grommet (106) when so rotated also increases, eventually becoming larger than the diameter of the opening (108) such that the grommet (106) can no longer pass through the opening (108) even when so rotated. In an embodiment, the arc-lengths of walls (114) and (116) is optimized to maximize the arc-lengths while still configuring the grommet (106) to pass through the opening (108).

In an alternative embodiment, the grommet (106) may be sized, shaped, and configured such that the largest arc-length of walls (114) and (116) is too large for the grommet (106) to be capable of being inserted through the opening (108) when rotated with respect to the opening as depicted in FIG. 5, unless the size and shape of the opening (108) is deformed or otherwise modified into a generally ellipsoid shape having a major axis large enough to accommodate the insertion of the grommet (106). This deforming or modification may be done through any means, including without limitation manual compression or squeezing.

In an embodiment, the angle of the arcs defining wall (114) is between 250 and 255 degrees, inclusive. In an embodiment, the angle of the arcs defining wall (114) is between 255 and 260 degrees, inclusive. In an embodiment, the angle of the arcs defining wall (114) is between 260 and 265 degrees, inclusive. In an embodiment, the angle of the arcs defining wall (114) is between 265 and 270 degrees, inclusive. In an embodiment, the angle of the arcs defining wall (114) is between 270 and 275 degrees, inclusive. In an embodiment, the angle of the arcs defining wall (114) is between 275 and 280 degrees, inclusive. In an embodiment, the angle of the arcs defining wall (114) is between 280 and 285 degrees, inclusive. In an embodiment, the angle of the arcs defining wall (114) is between 285 and 290 degrees, inclusive. In an embodiment, the angle of the arcs defining wall (114) is between 290 and 295 degrees, inclusive. In an embodiment, the angle of the arcs defining wall (114) is between 295 and 300 degrees, inclusive. In an embodiment, the angle of the arcs defining wall (114) is between 300 and 305 degrees, inclusive. In an embodiment, the angle of the arcs defining wall (114) is between 305 and 310 degrees, inclusive. In an embodiment, the angle of the arcs defining wall (114) is between 310 and 315 degrees, inclusive. In an embodiment, the angle of the arcs defining wall (114) is between 315 and 320 degrees, inclusive. In an embodiment, the angle of the arcs defining wall (114) is between 320 and 325 degrees, inclusive. In an embodiment, the angle of the arcs defining wall (114) is between 325 and 330 degrees, inclusive. In an embodiment, the angle of the arcs defining wall (114) is between 325 and 330 degrees, inclusive. In an embodiment, the angle of the arcs defining wall (114) is between 330 and 335 degrees, inclusive. In an embodiment, the angle of the arcs defining wall (114) is between 335 and 340 degrees, inclusive.

In an embodiment, the angle of the arcs defining wall (116) is between 250 and 255 degrees, inclusive. In an embodiment, the angle of the arcs defining wall (116) is between 255 and 260 degrees, inclusive. In an embodiment, the angle of the arcs defining wall (116) is between 260 and 265 degrees, inclusive. In an embodiment, the angle of the arcs defining wall (116) is between 265 and 270 degrees, inclusive. In an embodiment, the angle of the arcs defining wall (116) is between 270 and 275 degrees, inclusive. In an embodiment, the angle of the arcs defining wall (116) is between 275 and 280 degrees, inclusive. In an embodiment, the angle of the arcs defining wall (116) is between 280 and 285 degrees, inclusive. In an embodiment, the angle of the arcs defining wall (116) is between 285 and 290 degrees, inclusive. In an embodiment, the angle of the arcs defining wall (116) is between 290 and 295 degrees, inclusive. In an embodiment, the angle of the arcs defining wall (116) is between 295 and 300 degrees, inclusive. In an embodiment, the angle of the arcs defining wall (116) is between 300 and 305 degrees, inclusive. In an embodiment, the angle of the arcs defining wall (116) is between 305 and 310 degrees, inclusive. In an embodiment, the angle of the arcs defining wall (116) is between 310 and 315 degrees, inclusive. In an embodiment, the angle of the arcs defining wall (116) is between 315 and 320 degrees, inclusive. In an embodiment, the angle of the arcs defining wall (116) is between 320 and 325 degrees, inclusive. In an embodiment, the angle of the arcs defining wall (116) is between 325 and 330 degrees, inclusive. In an embodiment, the angle of the arcs defining wall (116) is between 325 and 330 degrees, inclusive. In an embodiment, the angle of the arcs defining wall (116) is between 330 and 335 degrees, inclusive. In an embodiment, the angle of the arcs defining wall (116) is between 335 and 340 degrees, inclusive.

When it is desired to remove the bag, such as when a procedure, examination or treatment is finished and the material in the storage bin (102) should be discarded or sanitized, the venting grommet (106) is likely to have biological or other material on its surface. As materials are discarded through the opening (108), a portion of the discarded material is likely to come in contact with a part of the venting grommet (106), particularly the interior wall (116), leaving a residue of material. Thus, for the system to remain sanitary, the venting grommet (106) itself may be sanitized or discarded and replaced with a sterile, clean grommet (106). As depicted in the embodiment of FIG. 5, the venting grommet (106) is removed from the rim (128) and inserted into the bag (200) within the storage bin (102) through the opening (108).

Although the outer circumference of the outer wall (116) is greater than that of the rim (128) defining the opening (108), the venting grommet (106) nevertheless can be inserted into the bag (200) through the opening (108) because of the arc shape of the grommet (106). That is, when the grommet (106) is rotated 90 degrees along an axis generally perpendicular to the plane of chord (118), the grommet (106) presents a narrower cross section than when the grommet (106) is oriented for attaching to the rim (128). This allows the grommet (106) to pass through the opening (108) into the bin (102) and/or bag (200). The bag (200) may then be removed from the bin (102) and discarded, or sent for sterilization, where the grommet (106) may be sterilized along with any tools or materials within the bag (200).

Because the rim (128) and the upper portion of the body of the storage bin (102) are protected by the bag (200), the storage bin (102) itself may not generally need to be cleaned, or may require only minimal cleaning and sterilization. The portions of the storage bin (102) that are difficult and time-consuming to clean, such as the threaded (104) rim (128), will not generally require cleaning because they were covered by a bag (200) and the venting grommet (106). This reduces costs and shortens the turnover time for the operating room and its equipment.

Figure 3:
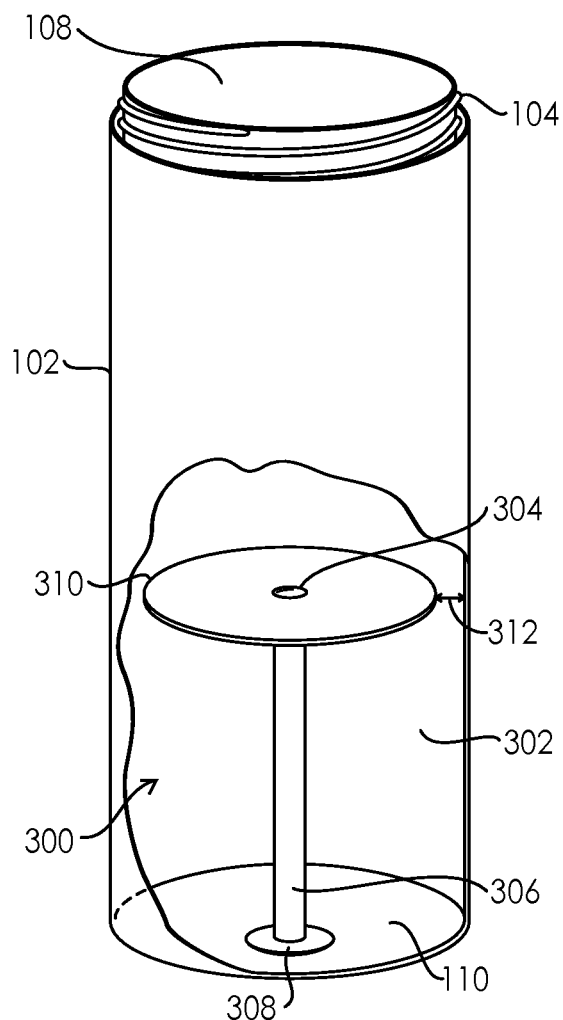
FIG. 3 provides a cross-section side view of an embodiment of a lined storage bin showing an embodiment of an internal bag spooling system.
Figure 4:
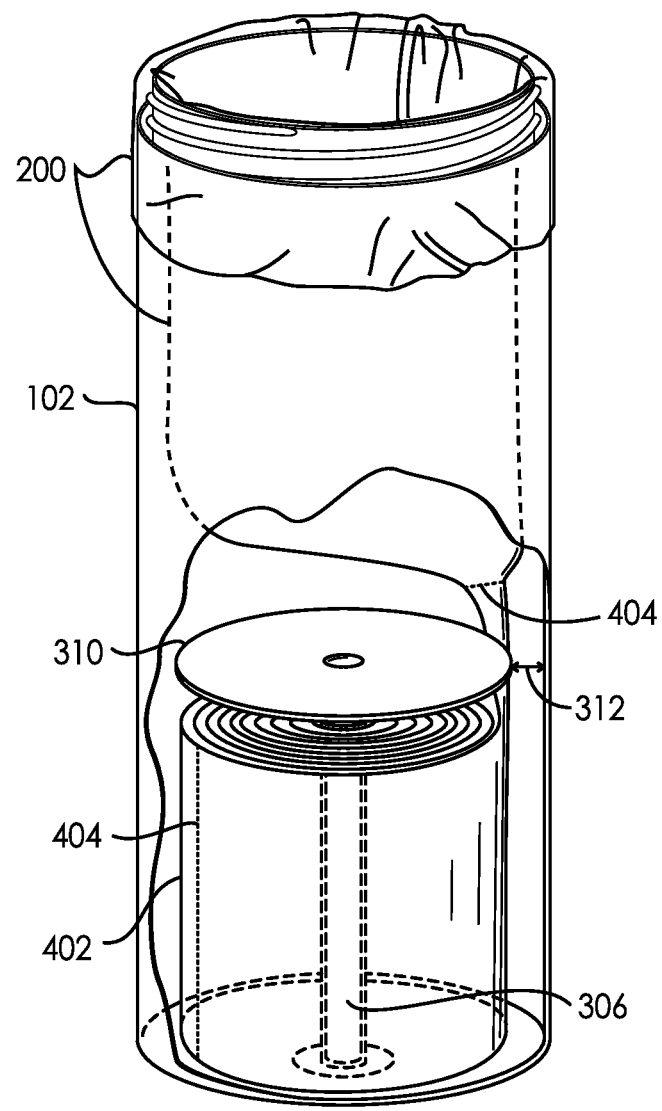
FIG. 4 provides a cross-section side view of an embodiment of a lined storage bin showing an embodiment of an internal bag spooling system, with a spool of bags attached thereto.

In an embodiment, the storage bin (102) is also sized and shaped for housing a bag and/or liner storage and/or dispensing system (300), such as depicted in FIGS. 3-4. In an embodiment, the storage bin (102) further includes a system (300) for storing and dispensing liner bags (200). In the depicted embodiment of FIG. 3, the system (300) includes a spindle (306) attached to a flat, disc-shaped support (310) at one end of the spindle (306) and oriented within the container (102) such that the central axis of the spindle (306) is generally collinear with the central axis of the storage container (102). The bottom of the spindle may be secured to the base (110) of the storage container (102) by a cap (308) which is affixed to the spindle (306) such as by use of adhesive, or hardware. The cap (308) in the depicted embodiment is attached to the exterior of the base (110) and passes through a hole in the base (110) to connect to the spindle (306). The top end of the spindle (306) generally is attached to the support (310) through the use of a second cap (304), which is attached to the spindle (306) in similar fashion to the bottom cap (308).

The support (310) provides a surface on which the bottom of the bag can rest. As materials are placed into the bag, the base (110) would ordinary provide a resting surface, but in an embodiment, including the depicted bag storage and retrieval system (300), the bottom of the bag (200) does not reach the base. Without a support (110), the bottom of the bag (200) would hang suspended within the bin (102), and as materials are accumulated in the bag (200), they would weigh it down, stretching and stressing the bag, and increasing the likelihood of a slip or tear. The support (310) relieves some of this pressure by providing a resting surface for accumulated material in the bag (200).

In the depicted embodiment, the disc is oriented such that the flat surface of the support (310) is generally parallel with the base (110) and opening (108). The diameter of the support (310) is generally sized and shaped such that a gap (312) exists between the outer ridge of the support (310) and the interior of the surface of the storage bin (102) and the gap (312) is wide enough to allow a bag (200) to pass through the gap (312). This arrangement is depicted in FIG. 4. In the embodiment of FIG. 4, a roll of bags (402) is placed on the spindle (306) and unraveled in part, with the unraveled bags being threaded through the gap (312). The topmost bag (200) has an open end which is disposed on the bin (102) as described elsewhere herein.

The spool of bags (402) may include, in an embodiment, a hollow tube at the middle of the spool through which spindle (306) is inserted, similar to bathroom tissue in a residential building. When the bag (200) is to be discarded, the bag (200) is removed from the bin (102) and sealed, such as by tying, zip tie, or other sealing system, and lifted out of the storage container (102). The roll of bags (402) initially includes a plurality of bags (200) connected to each other from bottom to top along a perforated edge (404). When the bag (200) in use is removed, the perforation (404) is torn, allowing the next bag in the spool (402) to be pulled from the container (102) and opened. By pulling on the top bag (200), the spool (402) will rotate about the spindle (306), allowing the next bag to pass through the gap (312) between the disc (310) and the inner wall of the container (102). In this fashion each bag (200) in the spool (402) may be used consecutively.

The bin (102) may be used independently or in a storage system, and may include further elements not depicted in the Figures. By way of example and not limitation, the bin (102) may include a system for attaching or hanging the bin (102) on equipment, such as a wall, table, gurney, bed, vehicle, chair, or other fixture or device. The bin (102) may also be sized and shaped for attaching to such equipment, such as by having a flat surface to reduce rolling.

In an embodiment, the bin (102) and/or grommet (106) are used in conjunction with a medical procedure, examination, or treatment, and the bin (102) and/or grommet (106) are sterilized and/or sanitized prior to the commencement of the medical procedure, examination, or treatment. In an embodiment, a bag (200) is disposed over the rim (128) and the grommet (106) is attached to the bin (102) before materials are placed in the liner bag (200). Materials are then placed in the bag (200) through the opening (108) of the bin (102) and the opening (122) of the grommet (106). The grommet (106) is then removed from the bin (102) before the bag (200) is removed from the bin, and the grommet (106) is inserted into the bag (200) through the opening (108) in the bin (102) while the bag (200) is still in the bin (102). Then, the bag (200) containing the grommet (106) is removed from the bin (102).

In an embodiment including a bag storage and dispensing system, such as the system depicted in FIGS. 3-4, after the bag (200) containing the grommet (106) is removed from the bin (102), another bag (200) is retrieved from the bag storage and dispensing system and disposed on the rim (128) as described elsewhere herein. A second grommet (106), or the cleaned and/or sterilized first grommet (106), is then attached to the bin (102).

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A storage bin comprising:
   a container comprising:
      a closed base end and an opposing open top end with an elongated body therebetween, said body having an interior side and an opposing exterior side and said open top end;
      a rim portion at said open top end forming the uppermost edge of said open top end and circumscribing a generally circular opening providing access to the interior of said enclosed container;
      wherein said exterior side comprises a first portion disposed around said rim and having a first radius a second portion disposed between said rim and said closed base end and having a second radius larger than said first radius;
      wherein said interior side has a height greater than said second portion;
   a venting grommet attachable to said open top end comprising:
      an outermost wall having opposing top and bottom sides and being generally in the shape of a circular major arc having two terminal ends, said outermost wall having a radius larger than the radius of said rim;
      an inner wall having opposing top and bottom sides and being generally in the shape of a circular major arc the endpoints of which are connected by a chord coplanar with said terminal ends of said outer wall, said inner wall having a radius smaller than the radius of said rim and said inner wall being generally concentric with and circumscribed by said outer wall, and said inner wall and said chord defining the perimeter of a hollow center opening;
      a top generally perpendicularly and terminally connected to said top side of said outer wall and said top side of said inner wall; and,
      wherein said inner wall and said outer wall are about the same height;
      wherein said inner wall, said outermost wall, and said hollow center opening are generally concentric;
      wherein when said venting grommet is attached to said open top end of said container, said outer wall only circumscribes a portion of said rim; and
      wherein when said venting grommet is rotated about ninety degrees with respect to said generally circular opening, said venting grommet can pass through said generally circular opening.

2. The storage bin as claimed in claim 1, said storage bin further comprising:
   a liner bag having an open end wherein when said liner bag is disposed upon said container such that said open end of said liner bag circumscribes said rim and when said venting grommet is attached to said container, said venting grommet holds said liner bag in place.

3. The storage bin as claimed in claim 1, wherein said rim and said outer wall are threaded such that said venting grommet may be screwed onto said rim.

4. The storage bin as claimed in claim 1, said storage bin further comprising:

a liner bag dispensing system comprising:
- a spindle within said container having opposing top and bottom ends and an elongated body therebetween, said bottom end of said spindle attached to the center of said base end of said container;
- a support within said interior having opposing top and bottom sides, said top end of said spindle being attached to said support;
- wherein when a spool of liner bags is placed on said spindle, a liner bag from said spool of liner bags can pass between said support and said interior side of said container.

5. The storage bin as claimed in claim 4, said storage bin further comprising a spool of liner bags disposed on said spindle.

6. The storage bin as claimed in claim 4, wherein the length of said spindle is less than half the length of said enclosed container.

7. The storage bin as claimed in claim 4, wherein said support is removable from said spindle.

8. The storage bin as claimed in claim 1, wherein the height of said inner wall is about the same as the height of said outer wall.

9. The storage bin as claimed in claim 1, where the radius of said rim is less than the radius of said cylindrical container.

10. The storage bin as claimed in claim 1, wherein said venting grommet is made from plastic.

11. The storage bin as claimed in claim 1, wherein the distance between the center of said chord and the midpoint of said major circular arc of said outer wall is greater than the radius of said rim and less than the diameter of said rim.

12. The storage bin of claim 1, wherein the angle measure of said major arc of said inner wall is not less than 250 degrees.

13. The storage bin of claim 1, wherein the angle measure of said major arc of said outermost wall is not less than 250 degrees.

* * * * *